US012099197B2

(12) United States Patent
Amitai

(10) Patent No.: US 12,099,197 B2
(45) Date of Patent: Sep. 24, 2024

(54) HEAD-MOUNTED DISPLAY EYEBALL TRACKER INTEGRATED SYSTEM

(71) Applicant: Lumus Ltd., Ness Ziona (IL)

(72) Inventor: Yaakov Amitai, Rehovot (IL)

(73) Assignee: LUMUS LTD., Ness Ziona (IL)

( * ) Notice: Subject to any disclaimer, the term of this patent is extended or adjusted under 35 U.S.C. 154(b) by 0 days.

(21) Appl. No.: 18/244,255

(22) Filed: Sep. 10, 2023

(65) Prior Publication Data
US 2023/0418069 A1 Dec. 28, 2023

Related U.S. Application Data

(63) Continuation of application No. 17/719,564, filed on Apr. 13, 2022, now abandoned, which is a continuation of application No. 16/731,275, filed on Dec. 31, 2019, now abandoned, which is a continuation of application No. 15/680,028, filed on Aug. 17, 2017, now Pat. No. 10,520,732, which is a
(Continued)

(30) Foreign Application Priority Data

May 21, 2012 (IL) .......................................... 219907

(51) Int. Cl.
| G02B 27/01 | (2006.01) |
| A61B 3/113 | (2006.01) |
| G02B 27/00 | (2006.01) |
| G02B 27/14 | (2006.01) |
| G02B 27/28 | (2006.01) |

(52) U.S. Cl.
CPC .......... *G02B 27/0172* (2013.01); *A61B 3/113* (2013.01); *G02B 27/0081* (2013.01); *G02B 27/0093* (2013.01); *G02B 27/0179* (2013.01); *G02B 27/141* (2013.01); *G02B 27/145* (2013.01); *G02B 2027/0125* (2013.01); *G02B 2027/0178* (2013.01); *G02B 2027/0187* (2013.01); *G02B 27/286* (2013.01)

(58) Field of Classification Search
CPC ............ G02B 27/0172; G02B 27/0081; G02B 27/0093; G02B 27/0179; G02B 27/145; G02B 27/286; G02B 2027/0125; G02B 2027/0178
USPC .......................................... 359/630; 345/156
See application file for complete search history.

(56) References Cited

U.S. PATENT DOCUMENTS

| 4,343,535 A * | 8/1982 | Bleha, Jr. ............. H04N 9/3167 349/9 |
| 2005/0140644 A1* | 6/2005 | Mukawa .................. G02B 5/32 345/156 |

(Continued)

FOREIGN PATENT DOCUMENTS

JP 2004233904 A 8/2004

*Primary Examiner* — Audrey Y Chang
(74) *Attorney, Agent, or Firm* — Rivka Friedman

(57) ABSTRACT

Head-mounted display with an eye-tracking system and including a light-transmitting substrate (20) having two major surfaces and edges, optical means for coupling light into said substrate (20) by total internal reflection, partially-reflecting surfaces (22a-22c) carried by the substrate (20) that are not parallel with the major surfaces of the substrate (20), a near-infrared light source (78) and a display source (92) projecting within the photopic spectrum, wherein light from the light source (78) and light from the display source (92) are coupled into the substrate (20) by total internal reflection.

2 Claims, 11 Drawing Sheets

Related U.S. Application Data continuation of application No. 14/399,113, filed as application No. PCT/IL2013/050428 on May 19, 2013, now Pat. No. 9,804,396.

(56) References Cited

U.S. PATENT DOCUMENTS

| | | |
|---|---|---|
| 2010/0067110 A1 | 3/2010 | Hadad et al. |
| 2013/0094712 A1 | 4/2013 | Said |
| 2013/0257832 A1* | 10/2013 | Hammond ........... G02B 6/0035 |
| | | 250/341.8 |

* cited by examiner

HEAD-MOUNTED DISPLAY EYEBALL TRACKER INTEGRATED SYSTEM

FIELD OF THE INVENTION

The present invention relates to integrated head-mounted display (HMD) systems, and in particular, to systems that include two combined units: a head-mounted unit and an eyeball tracking unit.

The invention can be implemented to advantage in a large number of imaging applications, such as portable DVDs, cellular phones, mobile TV receivers, video games, portable media players or other mobile display devices.

BACKGROUND OF THE INVENTION

One important application for compact optical elements, is in HMDs wherein an optical module serves both as an imaging lens and a combiner, in which a two-dimensional image source is imaged to infinity and reflected into an eye of an observer. The display source can be obtained directly from, e.g., a spatial light modulator (SLM) such as a cathode ray tube (CRT), a liquid crystal display (LCD), an organic light emitting diode array (OLED), a scanning source, or indirectly, by means of a relay lens, or an optical fiber bundle. The display source comprises an array of elements (pixels) imaged to infinity by a collimating lens and transmitted into the eye of a viewer by means of a reflecting or partially reflecting surface acting as a combiner for non-see-through and see-through applications, respectively. Typically, a conventional, free-space optical module is used for these purposes. As the desired field-of-view (FOV) of a HMD system increases, however, such a conventional optical module becomes larger, heavier and bulkier, and therefore, even for a moderate-performance device, is impractical. This is a major drawback for all kinds of displays and especially in head-mounted applications, wherein the system should necessarily be as light and compact as possible.

The strive for compactness has led to several different complex optical solutions, all of which, on the one hand, are still not sufficiently compact for most practical applications and, on the other hand, suffer major drawbacks in terms of manufacturability. Furthermore, the eye-motion-box (EMB) of the optical viewing angles resulting from these designs is usually very small, typically less than 8 mm. Hence, the performance of the optical system is very sensitive, even for small movements of the optical system relative to the eye of a viewer, and does not allow sufficient pupil motion for comfortable reading of text from such displays.

The teachings included in Publication Nos. WO01/95027, WO03/081320, WO2005/024485, WO2005/024491, WO2005/024969, WO2005/124427, WO2006/013565, WO2006/085309, WO2006/085310, WO2006/087709, WO2007/054928, WO2007/093983, WO2008/023367, WO2008/129539 and WO2008/149339, all in the name of Applicant, are herein incorporated by references.

DISCLOSURE OF THE INVENTION

The present invention facilitates the exploitation of very compact light-guide optical elements (LOEs) for, amongst other applications, HMDs. The invention allows for relatively wide FOVs together with relatively large EMB values. The resulting optical system offers a large, high-quality image, which also accommodates large movements of the eye. The optical system offered by the present invention is particularly advantageous because it is substantially more compact than the state-of-the-art implementations and yet, it can be readily incorporated even into optical systems having specialized configurations.

Another optical function which could prove to be useful for HMD designs is eyeball tracking, or sensing the direction the eyeball is looking at, relative to the direction of the head. A typical eye tracker will combine a miniature CCD camera and an infrared LED to illuminate the pupil. By measuring the changes in shape and position of the pupil, it is possible to perceive the direction in which the viewer's eye is looking, with very reasonable accuracy once calibrated. Combining measurements of head position and eye position would solve the problems inherent in existing HMD technology, since the projected symbols and boresight could be slaved to the direction in which the viewer is looking, thus retaining existing human tracking behavior. It will be useful to combine the HMD and the eyeball tracker in the same optical module.

A broad object of the present invention is therefore to alleviate the drawbacks of prior art compact optical display devices and to provide other optical components and systems having improved performance, according to specific requirements;

In accordance with the invention there is therefore provided an optical system, comprising a light-transmitting substrate having at least two major surfaces and edges, at least one optical means for coupling light waves into the substrate by total internal reflection, at least two partially reflecting surfaces carried by the substrate wherein the partially reflecting surfaces are not parallel to the main surfaces of the substrate, at least one light source projecting light waves located within a first optical spectrum, and at least one display source projecting light waves located within a second optical spectrum, characterized in that the light waves from the light source and light waves from the display source are coupled into the substrate by total internal reflection.

BRIEF DESCRIPTION OF THE DRAWINGS

The invention is described in connection with certain preferred embodiments, with reference to the following illustrative figures so that it may be more fully understood.

With specific reference to the figures in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention. The description taken with the drawings are to serve as direction to those skilled in the art as to how the several forms of the invention may be embodied in practice.

In the drawings:

FIG. 1 is a side view of an exemplary, prior art, LOE;

FIGS. 2A and 2B illustrate desired reflectance and transmittance characteristics of selectively reflecting surfaces, used in the present invention, for two ranges of incident angles;

FIG. 3 illustrates a reflectance curve as a function of the incident angle for an exemplary dielectric coating;

FIG. 4 is a schematic diagram illustrating a detailed sectional view of an exemplary array of selectively reflective surfaces;

FIG. 5 illustrates a prior art eyeglass HMD device;

FIG. 6 illustrates a side view of an LOE showing light waves scattered from an eye and coupled back into the LOE;

FIG. 7 illustrates a reflectance curve as a function of the wavelength for a specific partially reflecting surface;

FIG. 8 illustrates a reflectance curve as a function of the wavelength for another partially reflecting surface;

FIG. 9 illustrates reflectance curves as a function of the incident angle for two different partially reflecting surfaces;

FIG. 10 illustrates a side view of an LOE, showing light waves coupled out through an exit aperture, which are scattered from the eye and coupled back into the LOE;

FIG. 11 illustrates a side view of an LOE, showing light waves which are scattered from an eye and coupled back into the LOE, wherein only part of the rays are coupled out through an exit aperture;

Figure 12:
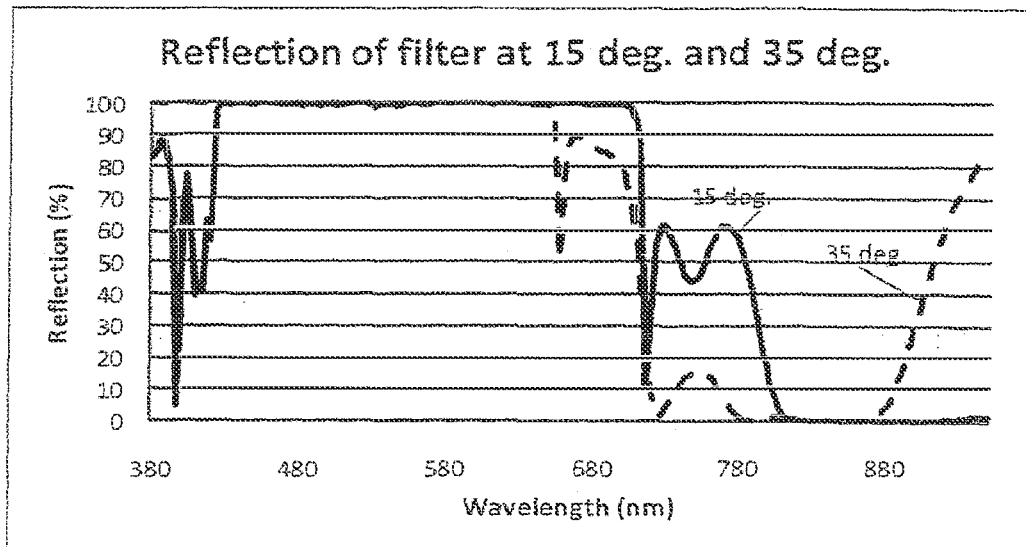
Figure 13:
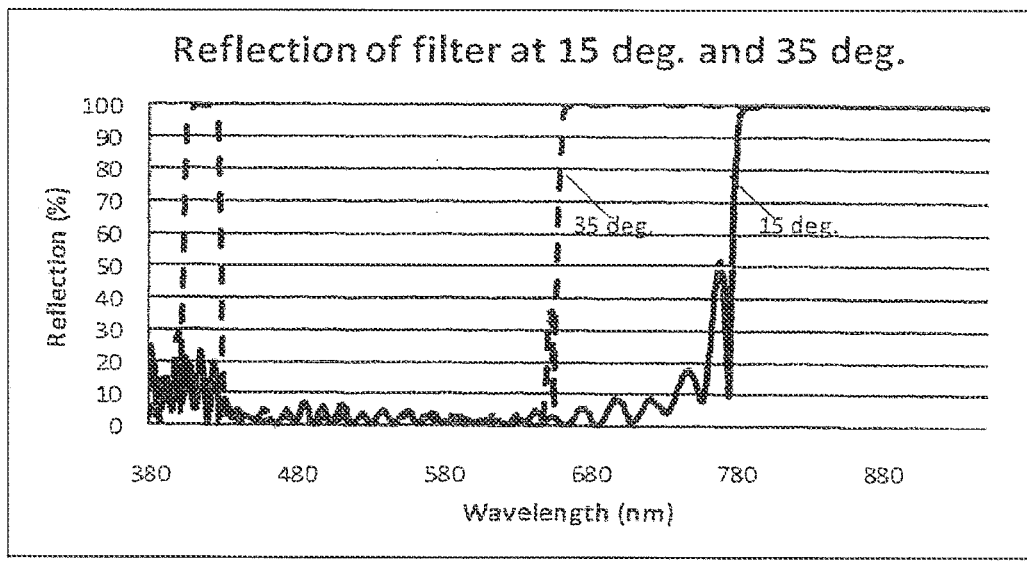
Figure 14:
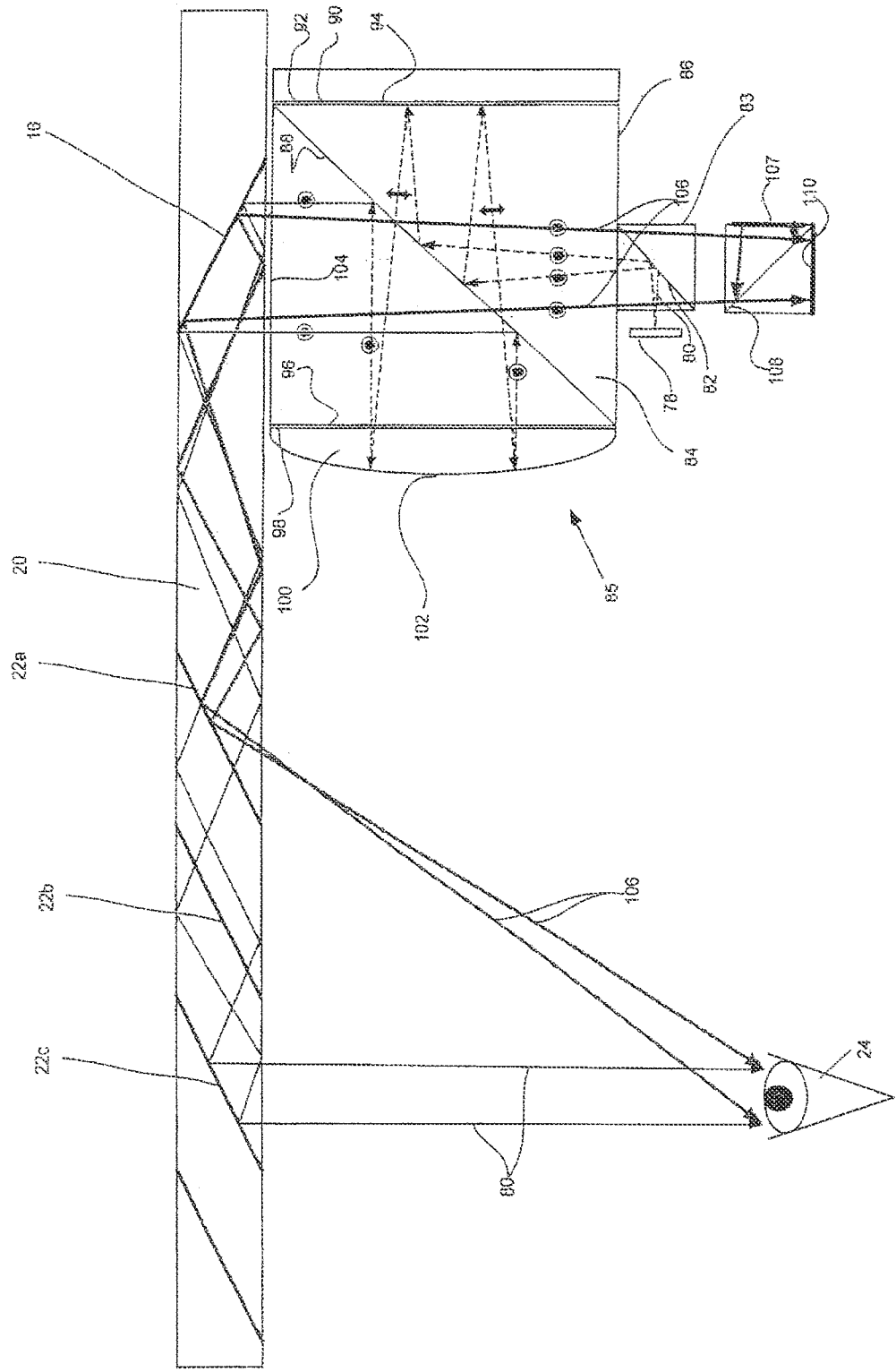
Figure 15:
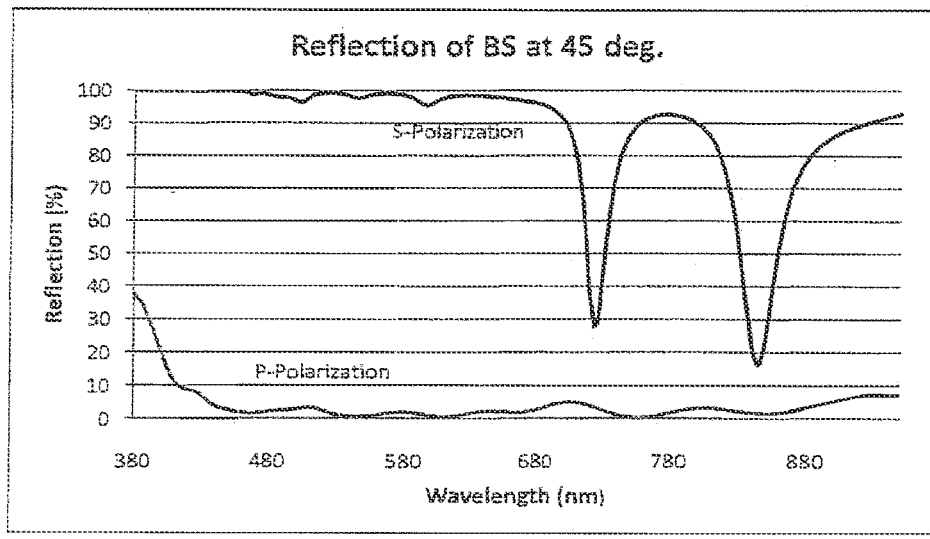
Figure 16:
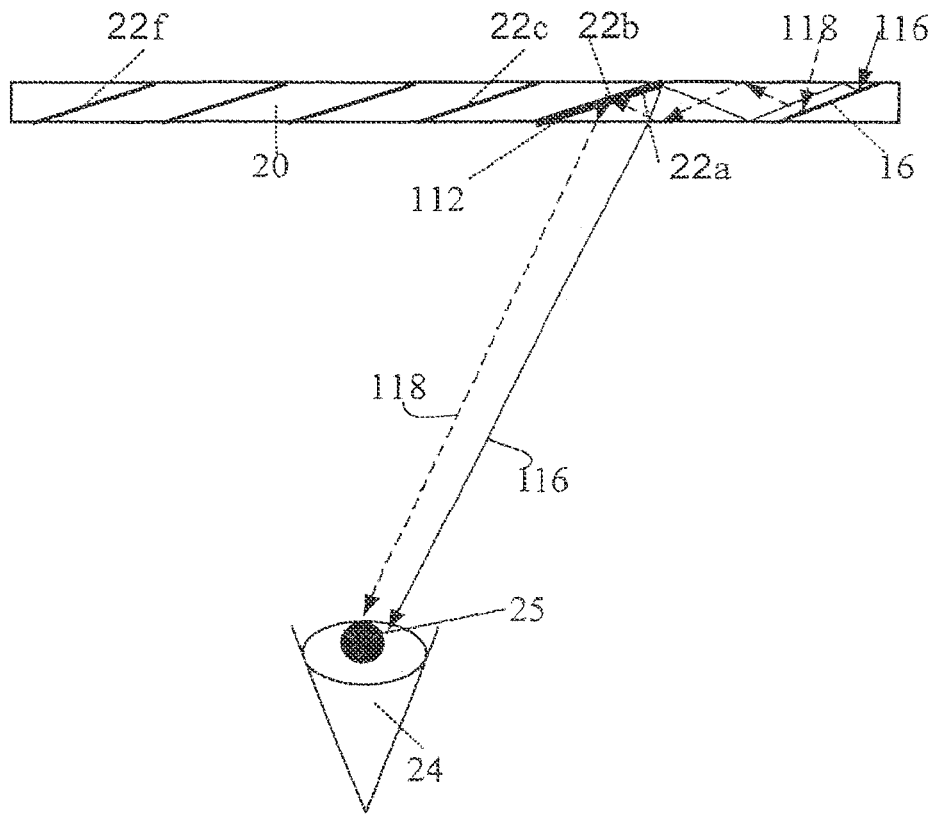

FIG. 12 illustrates reflectance curves as a function of the wavelength for a reflection filter at two different incident angles;

FIG. 13 illustrates reflectance curves as a function of the wavelength for a transmission filter at two different incident angles;

FIG. 14 illustrates an optical system combining light waves from a display source and a light source;

FIG. 15 illustrates a reflectance curve as a function of the wavelength for a polarizing beam splitter, and FIG. 16 illustrates a side view of still another embodiment of an LOE having two adjacent partially reflecting surfaces for coupling out light waves into the viewer's eye.

Figure 17:
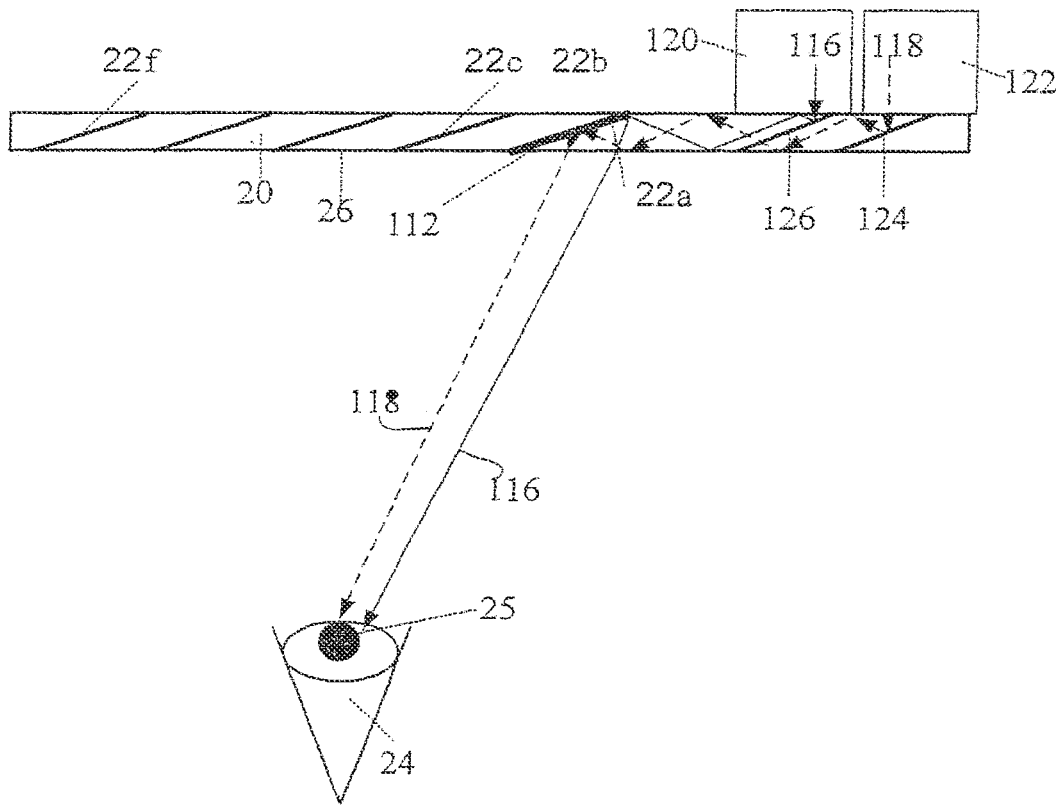

FIG. 17 illustrates a side view of another embodiment of an LOE having two separate coupling in elements.

Figure 18:
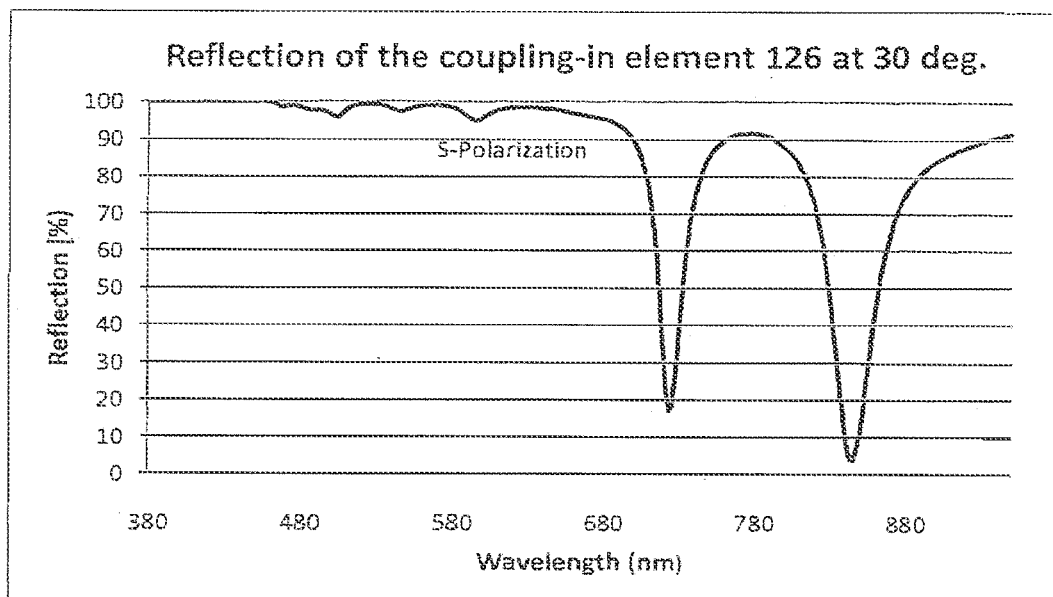

FIG. 18 illustrates a reflective pattern of the polarizing beam splitter of FIG. 17.

DETAILED DESCRIPTION OF PREFERRED EMBODIMENTS

Figure 1:
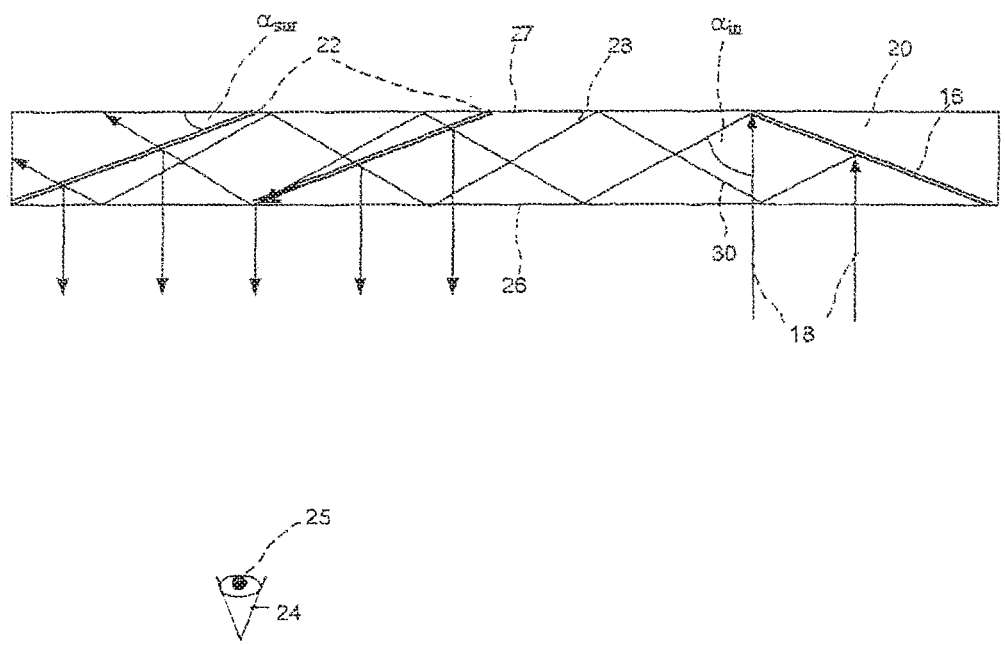

FIG. 1 illustrates a sectional view of a prior art substrate 20 and associated components (hereinafter also "an LOE"), utilizable in the present invention. An optical means, e.g., a reflecting surface 16, is illuminated by a collimated display 18, emanating from a light source (not shown) located behind the LOE. The reflecting surface 16 reflects incident light from the source, such that the light is trapped inside a planar substrate 20 of the LOE, by total internal reflection. After several reflections off the major lower and upper surfaces 26, 27 of the substrate 20, the trapped waves reach an array of selective reflecting surfaces 22, which couple the light out of the substrate into an eye 24, having a pupil 25, of a viewer. Herein, the input surface of the LOE will be regarded as the surface through which the input waves enter the LOE and the output surface of the LOE will be regarded as the surface through which the trapped waves exit the LOE. In the case of the LOE illustrated in FIG. 1, both the input and the output surfaces are on the lower surface 26. Other configurations, however, are envisioned in which the input and the image waves could be located on opposite sides of the substrate 20. Assuming that the central wave of the source is coupled out of the substrate 20 in a direction normal to the substrate surface 26, the reflecting surfaces 22 are flat, and the off-axis angle of the coupled waves inside the substrate 20 is $\alpha_{in}$ then the angle $\alpha_{sur2}$ between the reflecting surfaces and the normal to the substrate plane is:

$$\alpha_{sur2} = \frac{\alpha_{in}}{2}. \tag{1}$$

Figures 2A, 2B:
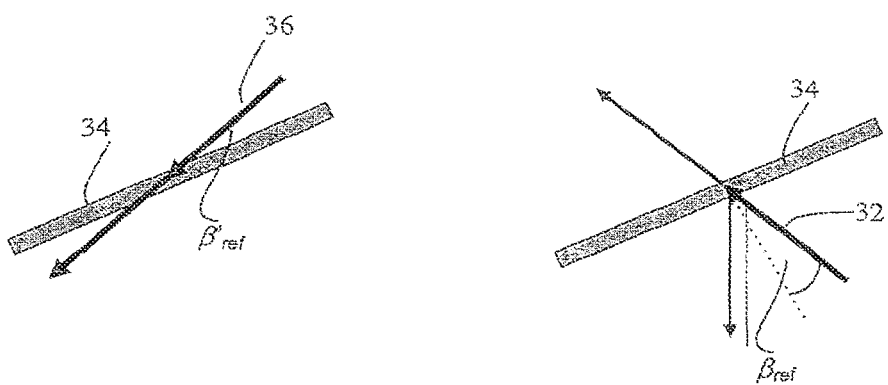

As seen in FIGS. 1 and 2A, the trapped rays arrive at the reflecting surfaces from two distinct directions 28, 30. In this particular embodiment, the trapped rays arrive at the reflecting surface from one of these directions 28 after an even number of reflections from the substrate surfaces 26 and 27, wherein the incident angle $\beta_{ref}$ (see FIG. 2A) between the trapped ray and the normal to the reflecting surface is:

$$\beta_{ref} = 90° - (\alpha_{in} - \alpha_{sur2}) = 90° - \frac{\alpha_{in}}{2}. \tag{2}$$

The trapped rays arrive at the reflecting surface from the second direction 30 after an odd number of reflections from the substrate surfaces 26 and 27, where the off-axis angle is a $\alpha'_{in}=180°-\alpha_{in}$ and the incident angle between the trapped ray and the normal to the reflecting surface is as indicated in FIG. 2B:

$$\beta'_{ref} = 90° - (\alpha'_{in} - \alpha_{sur2}) = 90° - (180° - \alpha_{in} - \alpha_{sur2}) = -90° + \frac{3\alpha_{in}}{2}. \tag{3}$$

As further illustrated in FIG. 1, for each reflecting surface, each ray first arrives at the surface from the direction 30, wherein some of the rays again impinge on the surface from direction 28. In order to prevent undesired reflections and ghost images, it is important that the reflectance be negligible for the rays that impinge on the surface having the second direction 28.

A solution for this requirement that exploits the angular sensitivity of thin film coatings was previously proposed in the Publications referred-to above. The desired discrimination between the two incident directions can be achieved if one angle is significantly smaller than the other one. It is possible to provide a coating with very low reflectance at high incident angles, and a high reflectance for low incident angles. This property can be exploited to prevent undesired reflections and ghost images by eliminating the reflectance in one of the two directions. For example choosing $\beta_{ref}\sim25°$, then it can be calculated that:

$$\beta'_{ref}=105°;\alpha_{in}=50°;\alpha'_{in}=130°;\alpha_{sur2}=25°. \tag{4}$$

If a reflecting surface is now determined for which $\beta'_{ref}$ is not reflected but $\beta_{ref}$ is, then the desired condition is achieved.

Referring now specifically to FIGS. 2A and 2B, these figures illustrate desired reflectance behavior of selectively reflecting surfaces. While the ray 32 (FIG. 2A), having an off-axis angle of $\beta_{ref}\sim25°$, is partially reflected and is coupled out of the substrate 34, the ray 36 (FIG. 2B), which arrives at an off-axis angle of $\beta'_{ref}\sim75°$ to the reflecting surface (which is equivalent to $\beta'_{ref}\sim105°$), is transmitted through the reflecting surface 34, without any notable reflection. An LOE is usually exploited not only for a single wave, but for an optical system having a wide FOV. Assuming a system having a FOV of 30° and an LOE having a refractive index of 1.517, then the FOV inside the substrate is ~20°. As a result, there are two angular regions which are defined for this specific LOE: a first region of 750±100 where $\beta'_{ref}$ is located, and a second region of 25°±10° where $\beta_{ref}$ is located.

Figure 3:
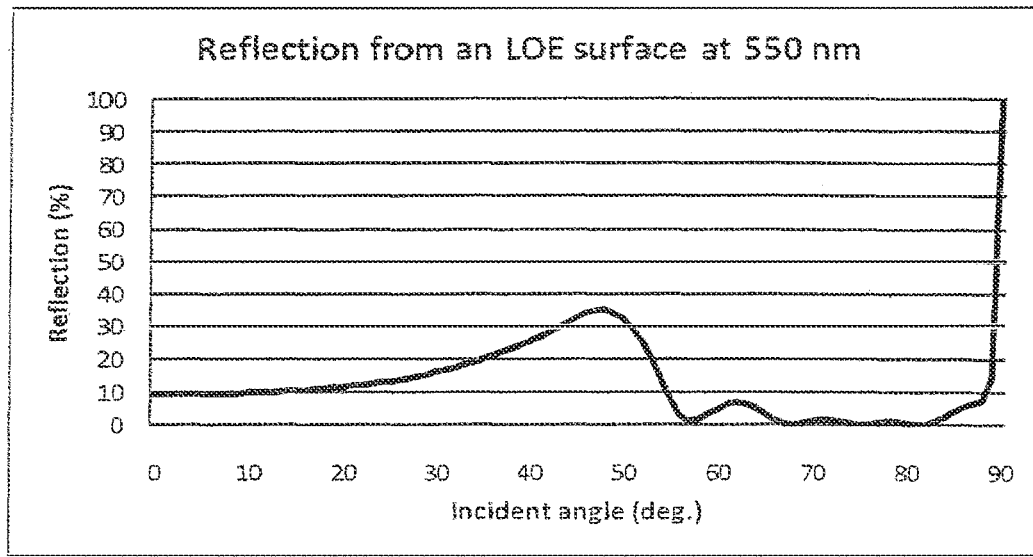

FIG. 3 illustrates the reflectance curve of a typical partially reflecting surface of this specific LOE, as a function of the incident angle for S-polarized light with the wavelength λ=550 nm. For a full-color display, similar reflectance curves should be achieved for all the other wavelengths in the photopic region. There are two significant regions in this graph: between 65° and 85°, where the reflectance is very low, and between 10° and 40°, where the reflectance increases monotonically with increasing incident angles. Hence, as long as, for a given FOV and for a given spectral region, it can ensured that the entire angular spectrum of $\beta'_{ref}$, where very low reflections are desired, will be located inside the first region, while the entire angular spectrum of $\beta_{ref}$, where higher reflections are required, will be located inside the second region, the reflection into the viewer's eye of an embodiment having only one substrate can be ensured, thus ensuring a ghost-free image.

Figure 4:
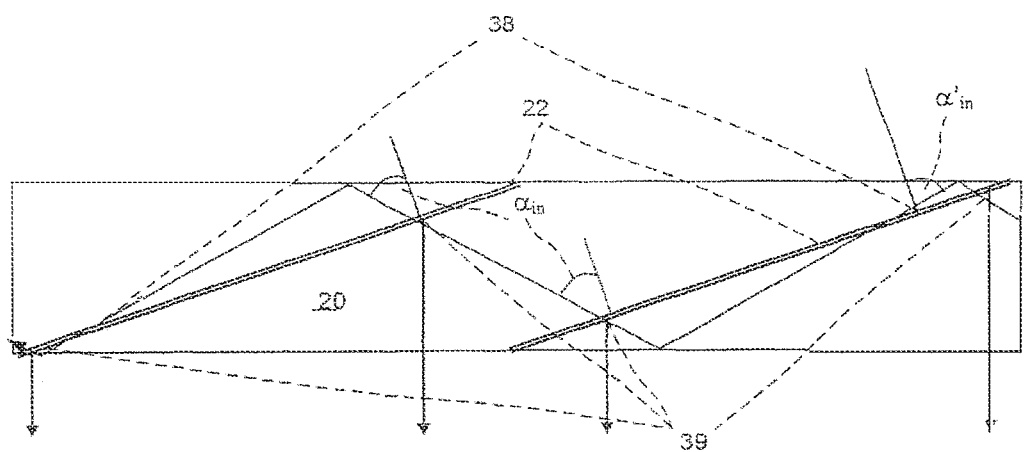

FIG. 4 is a schematic sectional view of an array of selectively reflecting surfaces which couple light rays trapped inside the substrate out and into an eye of a viewer. As can be seen, in each cycle, the coupled rays pass through reflecting surfaces 38, having a direction of $\alpha'_{in}=130°$, whereby the angle between the rays and the normal to the reflecting surfaces, is ~75°, and the reflections from these surfaces are negligible. In addition, in each cycle, the rays 39 pass through the reflecting surface 22 twice in a direction of $\alpha_{in}=50°$, where the incident angle is 25° and part of the energy of the ray is coupled out of the substrate.

In general, all the potential configurations of the LOEs considered in the Publications referred-to above, offer several important advantages over alternative compact optics for display applications, which include that:

1) the input display source can be located very close to the substrate, so that the overall optical system is compact and lightweight, offering an unparalleled form-factor;
2) in contrast to other compact display configurations, the LOE technology offers flexibility as to location of the input display source relative to the eyepiece. This flexibility, combined with the ability to locate the display source close to the expanding substrate, alleviates the need to use an off-axis optical configuration that is common to other display systems. In addition, since the input aperture of the LOE is much smaller than the active area of the output aperture, the numerical aperture of the collimating lens is much smaller than required for a comparable conventional imaging system. Consequently, a significantly more convenient optical system can be implemented and the many difficulties associated with off-axis optics and high numerical-aperture lenses, such as field or chromatic aberrations, can be compensated-for relatively easily and efficiently;
3) the reflectance coefficients of the selectively reflecting surfaces in the present invention, are essentially identical over the entire relevant spectrum. Hence, both monochromatic and polychromatic light sources may be used as display sources. The LOE has a negligible wavelength-dependence, ensuring high-quality color images with high resolutions;
4) since each point from the input image is transformed into a plane light wave that is reflected into the eye of a viewer from a large part of the reflecting array, the tolerances on the exact location of the eye can be significantly relaxed. As such, the viewer can see the entire FOV, and the EMB can be significantly larger than in other compact display configurations, and
5) since a large part of the intensity from the display source is coupled into the substrate, and since a large portion of this coupled energy is "recycled" and coupled out into an eye of a viewer, a display of comparatively high brightness can be achieved even with display sources having low-power consumption.

Figure 5:
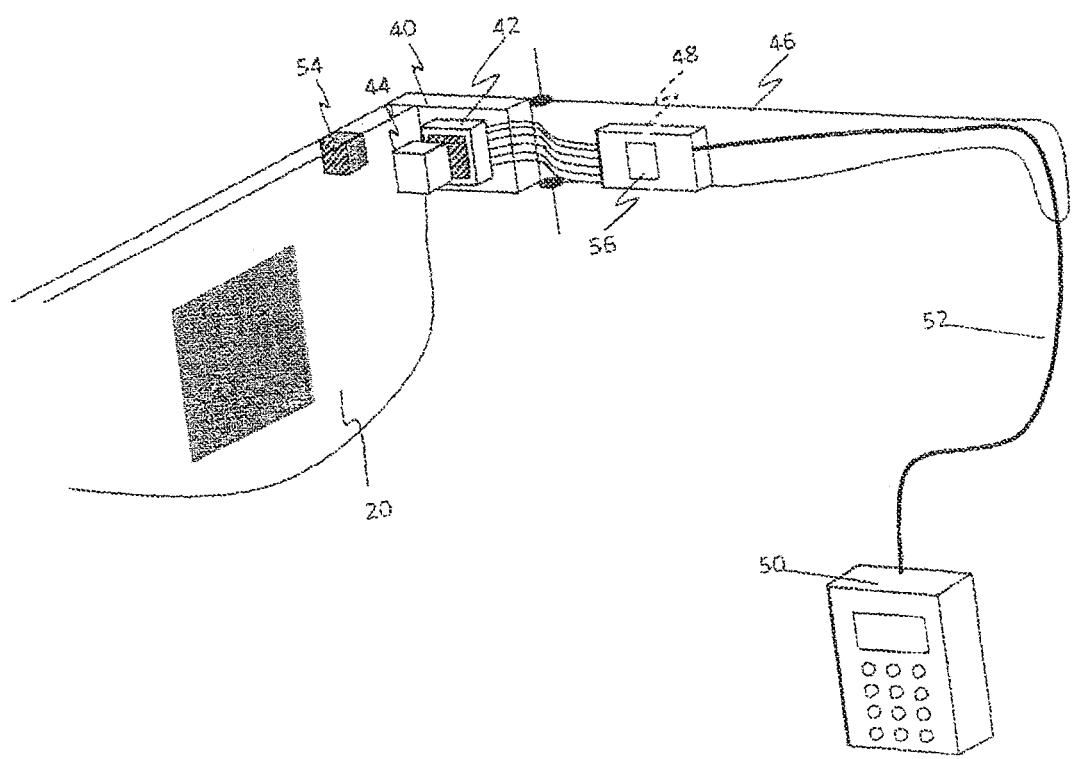

FIG. 5 illustrates a prior art embodiment in which the LOE is embedded in eyeglass frames 40. The display source 42 and the collimating device 44, which includes a light waves folding element, are assembled inside arm portions 46 of the eyeglass frames 40 next to the edge of the LOE. In a case where the display source is an electronic element, such as a small CRT, LCD or OLED, driving electronics 48 for the display source, may be assembled with the back portion of the arm 46. A handheld unit 50 comprising a power supply, a video source and control interface is connected to arm 46 by a cable 52, which is used for transmitting power, video signals, audio signals and control commands. Earphones can also be installed in the eyeglasses to enable the exploitation of audio channels. The handheld unit 50 can be a portable DVD, a cellular phone, a mobile TV receiver, a video games console, a portable media player, or any other mobile display device. The unit 50 is referred to as "handheld", since it is usually operated by the user's hand, but it can be any other portable device, and it can be affixed to the user's belt or located in a pocket, a pouch, a purse or hung on the user's neck. In addition to the components which are embedded in the eyeglass frame, a miniature video camera 54 with, optional optical zoom capability, can be installed e.g., in the front region of the frame 40. The camera captures images from the external scene, transfers the video signal to an image-processing unit 56, which can be installed inside the electronics unit 48, and controlled in real-time by the user. The processed image signal is then transferred to the display source 42 which projects the image through the LOE into the eye of a viewer. Other potential elements that can be installed on the frame are a GPS receiver, an orientation sensor and a coordinate position sensor, wherein the processor 56 receiving an input from these sensors is providing a visually sensible output for displaying on the eyeglass.

Some of the current HMD technology uses head position measurements to approximate line-of-sight, which may cause significant disparity between what a viewer is intended to look at, and what the viewer is actually looking at, as a result of at least ±20° eye movement. Therefore, it is necessary to integrate eyeball tracking capability into HMDs in some applications. Eyeball tracking is the process of measuring either the point of gaze or the motion of an eye relative to the head. An eyeball tracker is a device for measuring eye positions and eye movement. The most popular method for operating this device is by utilizing an optical method for measuring eye motion. Light from an external source, typically infrared, is reflected from the eye and sensed by a video camera, or some other specially designed optical sensors. The information is then analyzed to extract eye rotation from changes in reflections. Video-based eye trackers typically use corneal reflection and the center of the pupil as features to track over time. As a result, an HMD-eyeball tracker integrated system would be able to display stereoscopic virtual images as would a classical HMD, and also be able to track the 'direction of gaze' of a viewer.

In accordance with the present invention, it would be advantageous to physically combine the two optical units, the HMD and the eyeball tracker. Moreover, it would be beneficial to utilize the same LOE for projecting the light from the display source into a viewer's eye, as described above, as well as for illuminating the eye with light from the eye tracker source, and to collect light which reflects from the eye into the detector. These two optical units should work properly without interfering with each other. To achieve this goal, two main characteristics of the combined optical system are exploited in the present invention: a separate partially reflecting surface or facet, dedicated for transferring light from a light source to the inspected eye and backwards, and a light having a wavelength substantially different from the photopic region utilized for the eye tracking.

Figure 6:
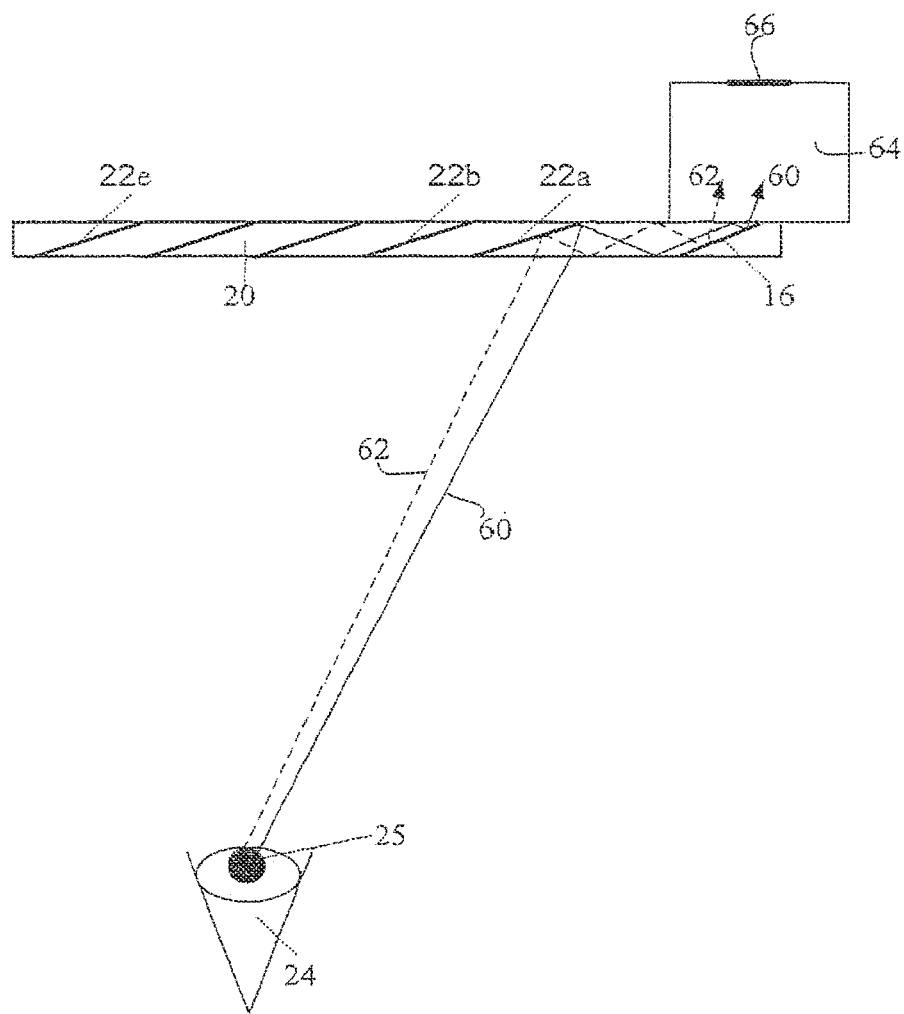

FIG. 6 schematically illustrates how one of the surfaces of an LOE can be utilized to illuminate the viewer's eye 24 for eye-tracking purposes. As illustrated, light rays from an eyeball tracker 64 having a wavelength of λtr, which is substantially different than the photopic region, usually in the near IR region and preferably at the range of 850-900 nm, are coupled into the LOE by total internal reflection through the light waves coupling surface 16. In this embodiment, the input and the image waves are located on opposite sides of the LOE. The light waves are coupled-out of the LOE by the partially reflecting surface 22a and are directed to illuminate the viewer's eye 24. After reflecting from the eye 24, rays 60 and 62 are coupled back into the LOE by the same partially reflecting surface 22a and then coupled-out of the LOE by the surface 16, back into the eye tracker 64, wherein light waves are imaged by a detector 66, which analyzes the incoming rays to track the position of the eye-pupil 25.

In order to avoid ghost images, it is important that only one of the facets of the surfaces of the LOE (partially reflecting surface 22a in the shown Figure) will reflect light waves in the range of about λir. Otherwise, light waves from other surfaces will also be reflected from the eye and cause a noise on the detector 66, thus severely degrading the quality of the imaged eyeball. In addition, reflecting surface 22a should be transparent to the photopic range in the relevant angular spectra of the LOE, in the lower region, as well as the upper one.

Figure 7:
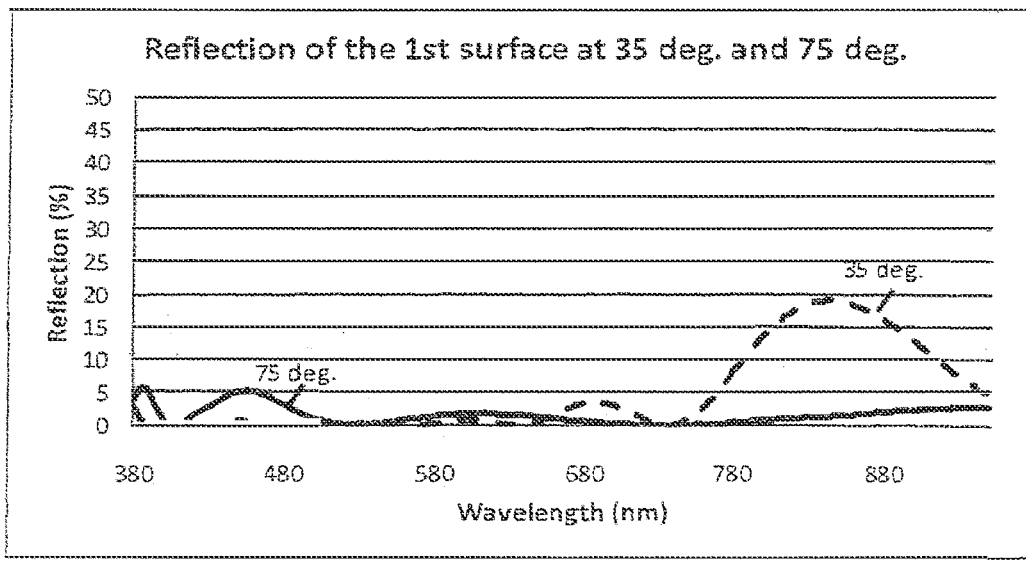
Figure 8:
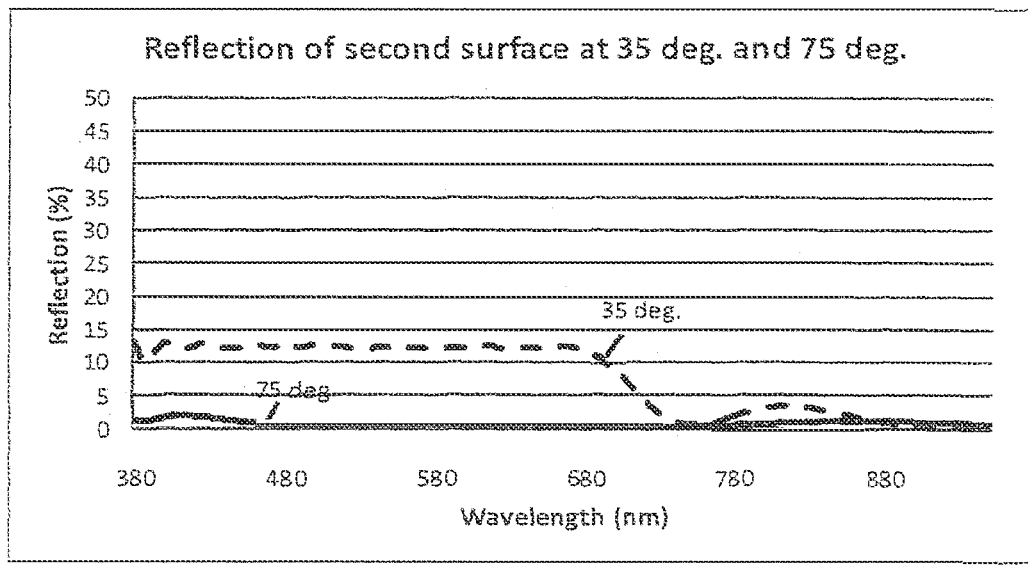

FIGS. 7 and 8 illustrate the reflectance curve of partially reflecting surfaces 22a and 22b, respectively, at incident angles of 35° and 75° as a function of the wavelength. As shown in FIG. 7, reflecting surface 22a reflects light waves having a wavelength of 850 nm with a reflectance of 20% at an incident angle of 35°, while it is actually transparent for the entire photopic range at both incident angles. At an incident angle of 35°, reflecting surface 22b partially reflects the light waves in the photopic range while it is actually transparent at an incident angle of 75° in the photopic range, as well as at both angles, in the region of 850 nm.

Figure 9:
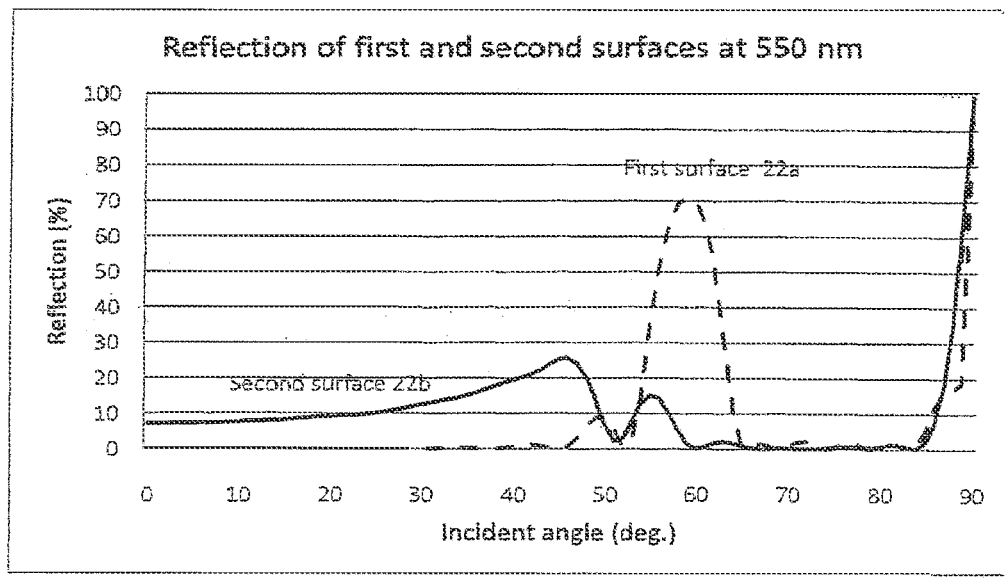

FIG. 9 illustrates the reflectance curve of partially reflecting surfaces 22a and 22b at a wavelength of 550 nm as a function of the incident angle. As illustrated, for surface 22b there are two significant regions in this graph: between 650 and 85°, where the reflectance is very low, and between 10° and 40°, where the reflectance increases monotonically with increasing incident angles, as required for the regular operation of an LOE. For partially reflecting surface 22a the reflectance is negligible at both lower and higher relevant angular regions. The actual interpretation of FIGS. 7 to 9 is that reflecting surface 22a is solely dedicated for eyeball tracking and does not at all interfere with the usual operation of the LOE at the photopic region. In addition, reflecting surface 22b is substantially transparent to the spectral region of around 850 nm, and hence, does not interfere with the optical operation of eyeball tracking. All the other partially reflecting surfaces are designed to behave in a similar manner to that of reflecting surface 22b. That is, the other facets are also transparent to the spectral region of 850 nm and have optical performance in the photopic region, as required by the optical design of the LOE acting as a combiner for HMD.

Figure 10:
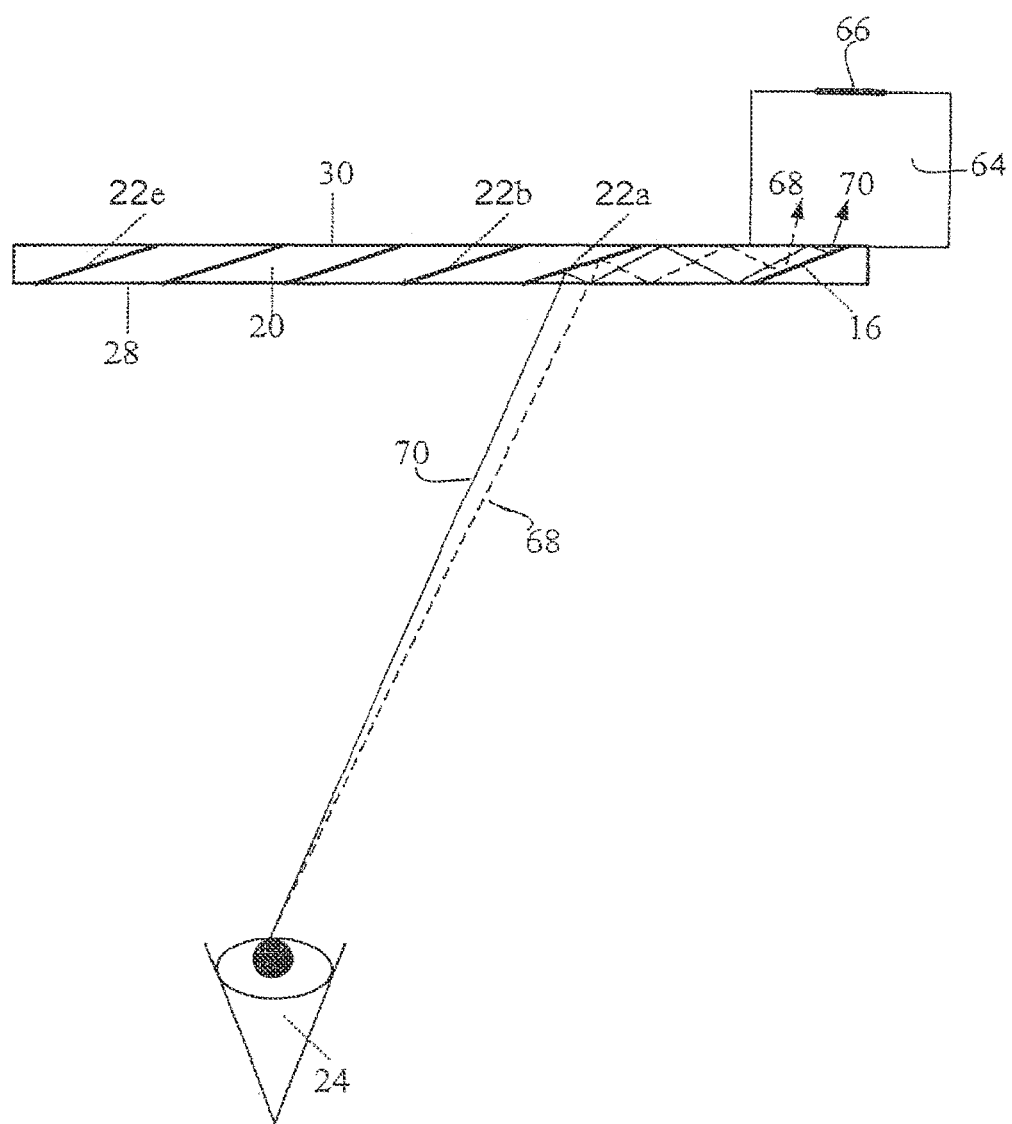

Another problem that should be addressed is the possibility that a ghost image might also for a single surface. As illustrated in FIG. 10, two different rays from a single point in the eye 24 are imaged through the LOE. Their optical behavior is, however, different: while ray 68 is reflected only once from each of the external surfaces 28 and 30 of the LOE, the ray 70 is reflected twice from each surface. As a result, these two rays have different optical pathways from partially reflecting surface 22a to reflecting surface 16, and hence, they cannot be utilized together to form the image of wavelength λout at the detector 66. Therefore, the rays that are reflected twice from the external surfaces 28, 30 must be blocked from the detector 66.

Figure 11:
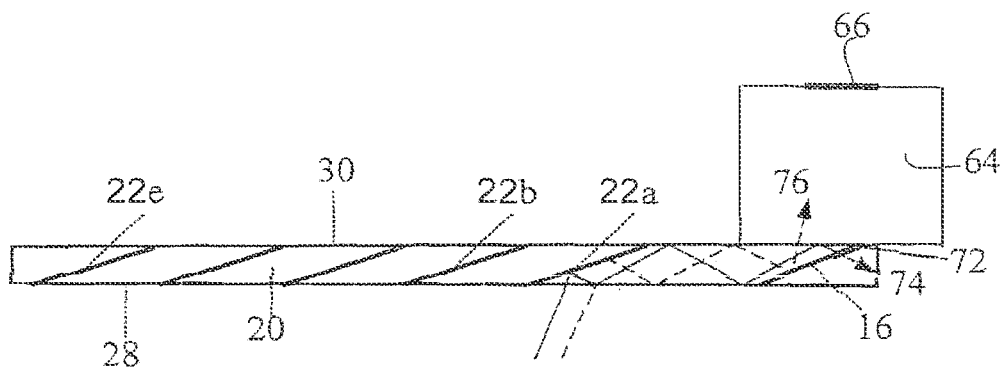

FIG. 11 illustrates how a spatial filter 72 which is located at the reflecting surface 16, blocks these undesired rays. That is, ray 74 is no longer reflected by surface 16 via tracker 64 into the detector 66, but rather continues to propagate inside the substrate, and is eventually absorbed at the edges of the LOE. In order to avoid disturbance for the incoming light waves from the display source which creates the image that is projected by the LOE into a viewer's eye, it is important that the filter 72 should be transparent to the light waves having a wavelength of λtr, while still being reflective to the photopic range.

FIG. 12 illustrates the reflectance curve of the filter 72 as a function of the wavelength at incident angles of 15° and 35°. As illustrated, the filter is highly reflective for the photopic range, while it is substantially transparent for the spectral range around 850 nm.

The embodiments described above with regard to the reflecting surface 16 are examples of a method for coupling the input waves into the substrate. Input waves could, however, also be coupled into the substrate by other optical means, including, but not limited to, folding prisms, fiber optic bundles, diffraction gratings, and other solutions. In some of these methods, which were described in the Publications referred to above, the input surface of the LOE is not a reflecting surface but rather a transparent aperture. In these cases, it is required that the filter will be reflective to light waves having a wavelength of tr, while still transparent to the photopic range.

FIG. 13 illustrates the reflectance curve of filter 72 as a function of the wavelength at incident angles of 15° and 35°. As illustrated, the filter 72 is substantially transparent for the photopic range, while it is reflective for the spectral range of about 850 nm.

The combination of a display source with a light source for illuminating an eye tracker utilizing light waves having a wavelength of λtr, is illustrated in FIG. 14. As shown, the s-polarized input light waves 80 emanating from the light source 78 and having wavelengths inside the photopic spectrum, are reflected by a reflective dichroic surface 82, e.g., a beam splitter, associated with a light guide 83, and are then coupled into a light guide 84 of a combiner 85, usually composed of a light waves transmitting material, through its lower surface 86. Following reflection of the light waves off of a polarizing beam splitter 88, the light waves are coupled out of the light guide 84 through surface 90. The light waves which illuminate bright pixels of the Liquid Crystal on Silicon (LCOS) 92 then pass through a dynamic quarter-wavelength retardation plate 94, reflected by a reflecting surface of the LCOS 92, return to pass again through the retardation plate 94, and re-enter the light-guide 84 through surface 90. The now p-polarized light waves pass through the polarizing beam splitter 88 and are coupled out of the light guide 84 through surface 96. The light waves then pass through a second quarter-wavelength retardation plate 98, collimated by a component 100, e.g., a lens, at its reflecting surface 102, return to pass again through the retardation plate 98, and re-enter the light-guide 84 through surface 96. The now s-polarized light-waves reflect off the polarizing beam splitter 88 and exit the light guide through the upper surface 104 of the combiner 85. In addition, s-polarized input light waves 106 having wavelengths of the light illuminating source 107, located in the eyeball tracker 108 and have an optical spectrum different than the photopic spectrum, preferably, in the near IR region, pass through the dichroic surface 82, are coupled into a light guide 84, pass directly through the polarizing beam splitter 88 and are then coupled out of the light-guide 84 through the upper surface 104. For the relevant angular spectrum, the dichroic surface 82 has high reflectance for the photopic spectrum and high transmittance for the spectrum of the light waves 106.

The two spectrally separated s-polarized input light waves 80 and 106 are now coupled through the reflecting surface 16 of the LOE, by total internal reflection. The light waves 80 are utilized for forming a virtual image projected by partially reflecting surfaces 22a-22e into a viewer's eye 24, while the light waves 106 are utilized to illuminate the eye 24 for eye-tracking. The light waves 106 having the wavelength of λtr, are reflected from the eye 24 coupled again into the LOE by the partially reflecting surface 22a, coupled out from the LOE through reflecting surface 16, and as seen, pass again through the polarizing beam splitter 88 and through the dichroic surface 82, and coupled into the eyeball tracker 108, where they are focused onto the detector 110.

FIG. 15 illustrates the reflectance pattern of the polarizing beam splitter 88 of FIG. 14. As shown, the beam splitter 88 has high and low reflectance, for the s- and p-polarization, respectively, in the photopic range, while having high transmittance for the s-polarized light having a wavelength of λtr.

In all the configurations described so far, the optical reflecting 16 is utilized to couple light waves from the display source having wavelengths in the photopic range, as well as light waves from the eyeball tracker 108 having wavelength of λtr, into the LOE, by total internal reflection. There are, however, configurations wherein different coupling elements are utilized to couple separately the light waves from the display source and the light waves from the eyeball tracker. These configuration include, but are not limited to, two different elements wherein the first one is substantially transparent for the photopic range, while it is reflective for the spectral range wavelength of λtr, and the second element is substantially transparent for the spectral range wavelength of λtr, while it is reflective for photopic range.

In all the configurations described so far, the two partially reflecting surfaces, 22a and 22b, are laterally separated. However, there are configurations wherein, for the sake of compactness or for enlarging the EMB of the optical system, it is required that the two surfaces will be adjacent to each other.

FIG. 16 illustrates a first partially reflecting surface 22a which is coated on the surface directed to one side of substrate 20, and a second partially reflecting surface 22b which is coated on the surface directed towards the other side of substrate 20. The two surfaces are optically attached and laterally separated by a cement layer 112. Typically, the thickness of the cement layer 112 is in the order of 10 μm, hence, the two surfaces can be considered as being optically disposed in one location. As illustrated, two different rays 116, 118 from the eyeball tracker 108 and the display source 92, respectively, (see FIG. 14) are coupled into the substrate 20 by the coupling reflecting surface 16 and then coupled out of the substrate 20 towards the viewer's eye 24 by partially reflecting surfaces 22a and 22b, respectively.

In all the hereinbefore described embodiments, the light waves from the eyeball tracker, as well as from the display source, are coupled into the substrate by the same coupling-in element. However, there are embodiments wherein, for the sake of simplicity or because of geometrical constraints, it is required that the eyeball tracker and the display source will be separated, and hence, the two different light waves will impinge on the substrate at two different locations.

FIG. 17 illustrates a system wherein the optical waves 116 and 118 from the eyeball tracker 120 and the display source 122, are separately coupled into the substrate 20 by two different coupling-in elements, 124 and 126, respectively. While the coupling-in element 124 is a simple reflecting surface, the coupling-in element 126 is a dichroic beam splitter. It is assumed that the angle between the surfaces 124 and 126 and the major surface 26 of the substrate 20 is about 30°.

FIG. 18 illustrates a reflection pattern of the polarizing beam splitter 126 of FIG. 17. As shown, the beam splitter 126 has high reflectance for the s-polarization in the photopic range at an incident angle of 30°, while having high transmittance for the s-polarized light having a wavelength of λtr at the same angle. As a result, light waves 116, having a wavelength of λtr, are coupled into the substrate by the reflecting surface 124 and then pass through the element 126 with negligible interference.

In some of methods described in the prior art Publications referred to above, the input surface of the LOE is not a reflecting surface, but rather a transparent aperture. In these cases, it is required that the second aperture will be reflective to light waves having a wavelength of λtr while still being transparent to the photopic range.

So far, it was assumed that the main purpose of the eyeball tracker is to measure eye positions and eye movements. When, however, an eyelid of a viewer's eye is closed, the pattern of the optical waves which are reflected from the eye, is significantly changed. The eyeball tracker can easily detect if a viewer's eyelid is open or closed. Since the LOE-based eyeglasses illustrated in FIG. 5 have a see-through capability, it is possible to utilize same for automotive applications where they can potentially assist a drive in driving and in navigation tasks, or can project a thermal image in the driver's eyes during low-visibility conditions. In addition to these tasks, the LOE-based eyeglasses, combined with an eyeball tracker, can also serve as a drowsy driver alert unit, that is, the eyeball tracker device can detect the driver's blinking patterns and determine how long the driver's eyes stay closed between blinks. Hence, the system can conclude that the driver is no longer alert and provide a warning concerning this situation.

What is claimed is:

1. An optical system for directing a projected image to an eye of a user and for directing infrared light employed for tracking the eye, the optical system comprising:
    (a) a lightguide optical element formed as a block of transparent material having a pair of mutually-parallel major external surfaces for guiding image light by internal reflection,
    (b) a plurality of image-deflecting surfaces located within said block of transparent material, said plurality of image-deflecting surfaces being mutually parallel, and being angled obliquely to said major external surfaces for coupling-out the image light towards the eye of the user, (c) an infrared-deflecting surface located within said block of transparent material for deflecting infrared light towards the eye of the user, and (d) a combination image projector and light source for introducing the projected image and infrared illumination via a common input aperture into said lightguide optical element, wherein said combination image projector and light source includes a polarizing beam splitter included in a prism, said prism having a first face for input of visible light illumination and infrared illumination, a second face provided with a polarization-modifying reflective spatial light modulator, a third face provided with a quarter-wave phase plate and reflective collimating optics, and an output face optically coupled to said common input aperture, and wherein said polarizing beam splitter is configured to direct visible light entering said first face to as to impinge sequentially on said polarization-modifying reflective spatial light modulator and said reflective collimating optics, and then to enter said common input aperture into said lightguide, and to direct said infrared illumination to said common input aperture without impinging on said polarization-modifying reflective spatial light modulator and said reflective collimating optics.

2. The optical system of claim 1, wherein said polarizing beam splitter is a chromatically-selective polarizing beam splitter implemented as a multi-layer dielectric coating configured to be:

(a) transparent to visible light having p polarization;

(b) reflective to visible light having s polarization; and (c) transmissive of a majority of the infrared illumination for both p-polarization and s-polarization.

* * * * *